United States Patent [19]

Matsui

[11] 4,417,875
[45] Nov. 29, 1983

[54] FOOT CONTROLLER FOR DENTAL INSTRUMENT

[75] Inventor: Takahiro Matsui, Uji, Japan

[73] Assignee: Kabushiki Kaisha Morita Seisakusho, Kyoto, Japan

[21] Appl. No.: 249,386

[22] Filed: Mar. 31, 1981

[30] Foreign Application Priority Data

Dec. 2, 1980 [JP] Japan .......................... 55-173377[U]

[51] Int. Cl.³ .............................................. A61C 1/02
[52] U.S. Cl. .................................. 433/101; 200/153 C
[58] Field of Search ................... 433/101; 200/153 C; 251/295; 318/551; 74/512, 513, 514

[56] References Cited

U.S. PATENT DOCUMENTS

| 562,116 | 6/1896 | Bryant | 200/153 C |
|---|---|---|---|
| 2,535,021 | 12/1950 | Stone et al. | 200/153 C |
| 3,623,693 | 11/1971 | Hill | 251/295 |
| 3,855,704 | 12/1974 | Booth | 433/101 |
| 3,963,391 | 6/1976 | Thorburn et al. | 251/295 |
| 4,043,041 | 8/1977 | Hornick | 433/101 |
| 4,118,866 | 10/1978 | Ross et al. | 433/101 |
| 4,172,217 | 10/1979 | Miller | 200/153 C |

FOREIGN PATENT DOCUMENTS 2715798 10/1978 Fed. Rep. of Germany ...... 433/101

Primary Examiner—John J. Wilson
Attorney, Agent, or Firm—Koda and Androlia

[57] ABSTRACT

A foot controller for controlling dental instruments of the type including pedals for controlling the rotational speed of a handpiece. The foot controller is designed such that the front part of the pedal is used for controlling high-speed rotation and requires a small tread pressure; while the rear portion of the pedal is to be used for controlling low-speed rotation and requires a large tread pressure.

1 Claim, 5 Drawing Figures

FOOT CONTROLLER FOR DENTAL INSTRUMENT

BACKGROUND OF THE INVENTION

1. Field of the Invention

The present invention relates to foot controllers for dental instruments.

2. Prior Art

In the prior art, this type of foot controller has been equipped with one or two pedals for controlling the rotational speed of the dental handpiece. For filling a tooth, the rotational speed must be adjusted by controlling the foot pressure in accordance with the position being filled and the filling accuracy. Usually, high-speed is utilized for rough filling (rasping) while the low-speed is used for high precision filling. When filling a tooth of a patient lying on his back on a bed, while the operator is sitting on a chair, as in the case of sedentary treatment, because of the operating posture, the operator's foot is automatically stretched forward (to a position in front of and away from the chair where the therapist is sitting) during the rasping by high rotational speed. On the contrary, during precision filling with slower rotation, the operator's foot is automatically placed at a position near the chair.

In this case, in the prior art foot controller, the tread turning position of the operating pedal is fixed to be around the center area. Therefore, care must be taken to move the foot controller itself to a position in front of and away from the chair during rasping while during precision drilling, to move it reversely to a position closer to the chair. Furthermore, during rough filling, the pedal must be stepped on hard in order to provide the high-speed rotation at the point away from and in front of the chair. Combined with the increase in spring tension of the pedal, this operating position intensifies the operator's fatigue with increase in rasping time.

SUMMARY OF THE INVENTION

Accordingly, it is a general object of the present invention to provide a foot controller wherein it is easy to shift the operator's foot position for control of the rotational speed of the dental handpiece during filling for both rough and precision filling of a tooth.

It is another purpose of the present invention to provide a foot controller that reduces operater fatigue even during rasping work, which takes a relatively long time.

In keeping with the principles of the present invention, the objects are accomplished by a unique foot pedal. The foot pedal is designed such that the front part of the pedal provides high-speed rotational control and requires a small foot pressure, while the rear part of the pedal is used for low-speed control and requires a large foot pressure.

BRIEF DESCRIPTION OF THE DRAWINGS

The above mentioned features and objects of the present invention will become more apparent with reference to the following description taken in conjunction with accompanying drawings, wherein like reference numerals denote like elements and in which.

DETAILED DESCRIPTION OF THE INVENTION

Figure 1:
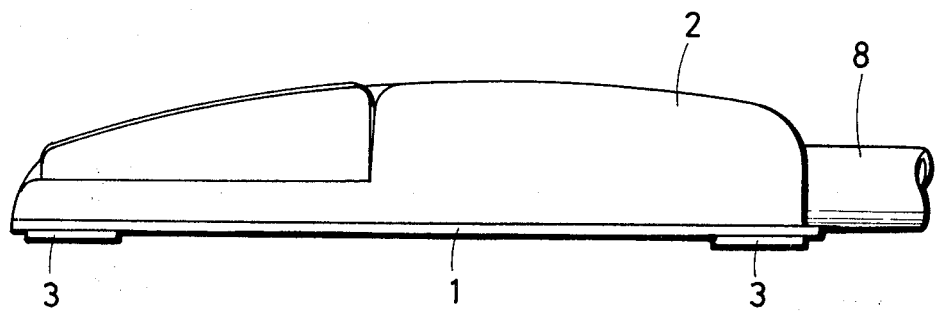
FIG. 1 is a front view of a foot controller in accordance with the teachings of the present invention.
Figure 2:
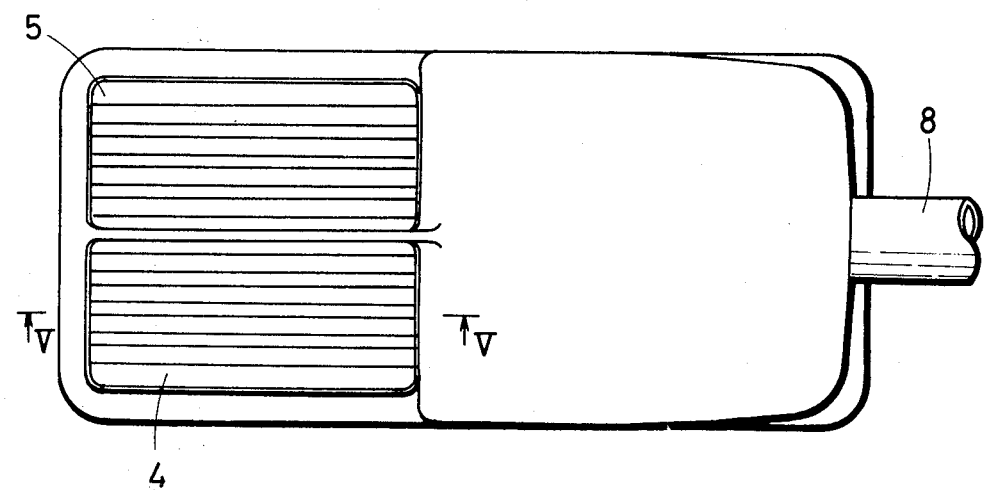
FIG. 2 is a top plan view of FIG. 1.
Figure 3:
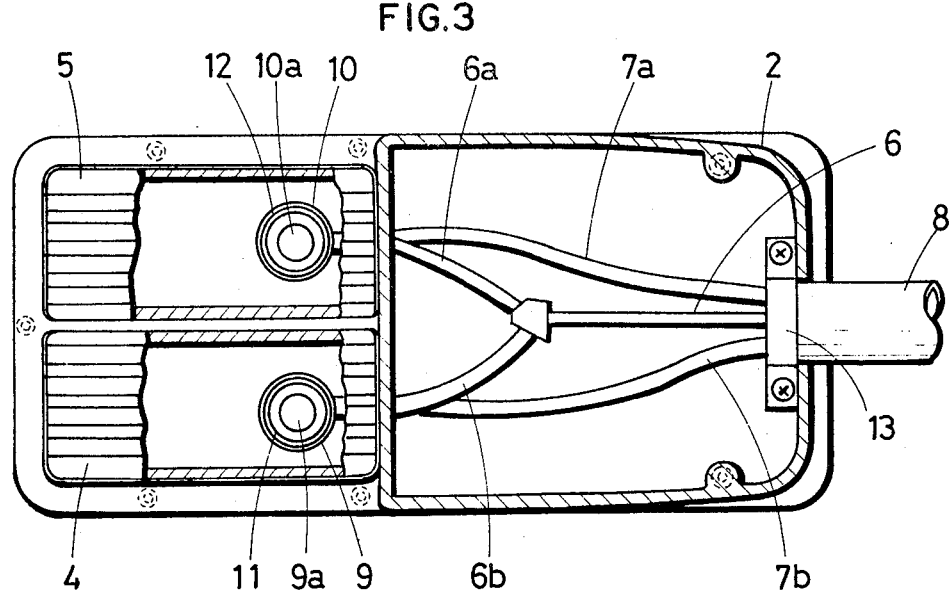
FIG. 3 is a partially cut away top plan view of the foot controller of FIG. 1.
Figure 4:
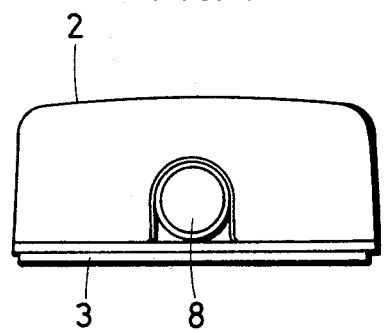
FIG. 4 is a side view of the foot controller of FIG. 1.
Figure 5:
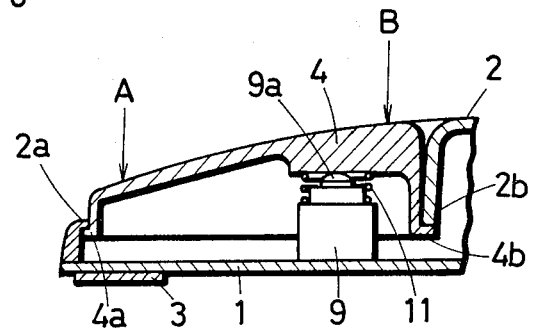
FIG. 5 is a section taken along the line V—V in FIG. 1.

Referring more particularly to the drawings, the foot controller of the present invention is provided with a pedal 4 for controlling the rotational speed of the low-speed air turbine handpiece and a pedal 5 for controlling the rotational speed of the ultra-high speed air turbine handpiece. As is shown in FIG. 5, the pedal 4 engages, by its bent rear edge 4a, with the flanged rear edge 2a of the pedal fitting opening of the cover 2. Also, the pedal 4 engages, by its bend front edge 4b, with the front pensile edge 2b of the pedal fitting opening of the cover 2. Furthermore, the pedal 4 is installed in manner to constantly receive a upward pressure by the spring 11 from the underside. With such a structure, when the front part B of pedal 4 is pressed upon with the foot, the pedal 4 rotates about the bent rear edge 4a which engages with the flanged edge 2a of the cover 2 opening; while conversely, when the rear part A is stepped on, the pedal 4 rotates about the bent front edge 4d which engages with the pensile front edge 2b of the cover 2 opening.

Provided on the back side of the front part B of the pedal 4 is an air valve 9 which also functions as the resting base for the spring 11. The valve 9 is fixed to the base 1 such that the upper end of the valve rod 9a of the valve 9 contacts the backside of the pedal 4. The valve 9 adjusts the air pressure supply to the air turbine handpiece by controlling the amount of the valve rod 9a depressed. As is shown in FIG. 5, the valve 9 is designed such that when the valve rod 9a is in the projecting state, the valve is closed; but when the valve rod 9a is depressed all the way in, the valve 9 becomes fully opened.

With such a structure since the valve 9 is provided on the underside of the front part B of the pedal 4 and as a result of the different leverages, the foot pressure to actuate the valve 9 on the rear part A is reduced relative to the foot pressure to actuate the valve 9 on the front part B. Through this arrangement, the front part B of the pedal is used as the operating section for high-speed rotation so as to control the high-speed rotation of the handpiece by causing the valve 9 to fully open even with a light step on the foot pedal. Also, the rear part A of the pedal is used to serve as the portion controlling the low-speed rotation. As a result, high-speed and low-speed control by way of controlling the length of the valve rod 9a of the valve 9 is facilitated.

It should be apparent that if the handpiece is a motor driven type, instead of using a valve 9, for example, a variable resistor could be utilized. In addition, since the structure of the other pedal 5 is the same as that of the pedal 4, an explanation of its construction and operation is omitted.

In addition to the above elements, the foot pedal includes a slip guard 3 on the base 1, an air supply tube 6, an air supply tube 6a for the air supply tube for the handpiece valve 9, air supply tube 6b for the handpiece valve 10, tubes 7a and 7b connected to the outlet portions of the valves 9 and 10, a piping tube 8 for containing the tubes extending from the base 1 and a fixture 13 for connecting the tube 8 to the base 1.

From the above description it should be apparent that in the foot controller of the present invention, the front part B of the respective pedals 4 and 5 is designed to serve as the controlling portion for high-speed rotation; while the rear part A is utilized to control the low-speed rotation. Therefore, if the foot pedal is provided at the proper position, it requires only a slight foot pressure on the front portion B of the pedal 4 or 5 for rasping during high-speed rotation. On the contrary, for precision filling by controlling the rotational speed, the pedal of the present invention requires only pressure on the rear portion A of the pedal 4 or 5 to control the rotational speed and such pressure can be provided by the tip of the foot placed nearby the chair. Thus, different from conventional foot controllers, the foot controller of the present invention is convenient since one is not required to move the foot controller forward and rearward everytime the speed changes. In addition, during rasping, the foot controller of the present invention requires only a light foot pressure on the front part B of the pedal 4 or 5 and thus the operator does not get tired even if the rasping work continues for a long time.

It should be apparent that it would be possible to design the foot pedal of the present invention to have adjustable foot pressure. In other words, some mechanism could be provided for adjusting the spring tension and/or the structure of the foot pedal housing itself could be adjustable to vary the leverages.

It should be apparent to those skilled in the art that the above described embodiment is merely illustrative of but one of the many possible specific embodiments which represent the principles of the applications of the present invention. Numerous and various other arrangements can be readily devised by those skilled in the art without departing from the spirit and scope of the present invention.

I claim:

1. A foot controller for a dental instrument comprising:
   a base;
   a foot controller cover provided on said base;
   a pair of pedal fitting openings provided in said foot controller cover adjacent each other;
   a flanged rear edge provide in each pedal fitting opening;
   a front pensile edge provided in each pedal fitting opening;
   a pedal provided in each of said pedal fitting openings;
   a bent rear edge provided on each pedal for engagement with said flanged rear edges;
   a bent front edge provided on each pedal for engagement with said front pensile edges;
   a pair of air valves provided on said base, each of said air valves being provided subjacent one of said pedals, said air valves further being provided closer said front pensile edge than said flanged rear edge;
   a valve rod extending from each of said air valves and engaging an undersurface of one of said pedals; and
   a spring surrounding each of said valve rods and engaging said undersurface of each of said pedals for upwardly biasing each of said pedals.

* * * * *